United States Patent [19]
Campbell

[11] Patent Number: 5,416,079
[45] Date of Patent: May 16, 1995

[54] 21-CHLORO-PREGNANE DERIVATIVE
[75] Inventor: Alexander C. Campbell, Falkirk, Scotland
[73] Assignee: Akzo N.V., Arnhem, Netherlands
[21] Appl. No.: 96,327
[22] Filed: Jul. 22, 1993
[30] Foreign Application Priority Data
  Jul. 22, 1992 [EP] European Pat. Off. ............ 92306697
[51] Int. Cl.⁶ ........................ C07J 43/00; A61K 31/58
[52] U.S. Cl. ........................................ 514/176; 540/95
[58] Field of Search ........................... 540/95; 514/176
[56] References Cited
U.S. PATENT DOCUMENTS
  3,225,034 12/1965 Hewett et al. .................... 260/239.5

Primary Examiner—Nicholas Rizzo
Attorney, Agent, or Firm—William M. Blackstone

[57] ABSTRACT

The invention is related to a 21-chloro-pregnane derivative of the formula

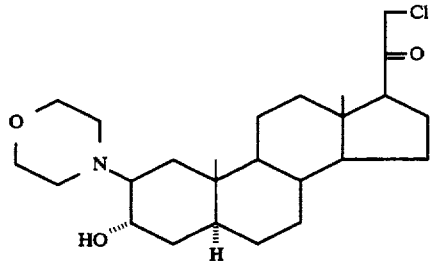

or pharmaceutically acceptable salts thereof. The compound has intravenous anaesthetic activity, short onset time and high potency.

3 Claims, No Drawings

21-CHLORO-PREGNANE DERIVATIVE

The invention relates to a 21-chloro-pregnane derivative, a process for its preparation, a pharmaceutical composition containing the same, as well as to its use for application as an intravenous anaesthetic drug.

Pregnane derivatives having intravenous anaesthetic activity are known in the art. The reference compound in this respect is Alphaxalone, an 11-keto pregnane derivative of the formula I, wherein $R_1$ and $R_3$ are hydrogen, and $R_2$ is oxygen:

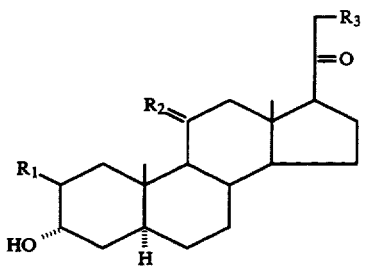

Attempts to improve the hypnotic activity of this reference drug have been undertaken, for example in British Patent 902,254 by introduction of a 21-halogen substituent (formula I, $R_3$ is halogen). It was found, however, that the 21-chloro derivative of Alphaxalone ($R_1$ is hydrogen, $R_2$ is oxygen, and $R_3$ is chlorine) is convulsant. The deletion of the 11-oxo group ($R_2$ is $H_2$) led to compounds with decreased hypnotic activity, whereas introduction of the 21-chloro substituent together with 11-reduction ($R_1$ is hydrogen, $R_2$ is $H_2$, and $R_3$ is chlorine) decreased the activity further. In a different attempt to improve the properties, 2β-amino steroids, and in particular 2β-morpholino steroids, were proposed in U.S. Pat. No. 3,225,034. This attempt was not very successful, because the 2β-morpholino derivative of Alphaxalone (formula I: $R_1$ is morpholino, $R_3$ is hydrogen, and $R_2$ is oxygen) was found to be more than three times less active than Alphaxalone itself. On the basis of these results it appears that neither 21-chloro substitution, 11-reduction, nor introduction of a 2β-morpholino group leads to useful compounds.

Surprisingly it was now found that the combination of all of these, as such unfavourable, modifications of the Alphaxalone structure leads to a very potent compound with fast onset, favourable therapeutic index, and strong hypnotic activity. This is even more remarkable because rat data showed that the same combination with the 21-bromo rather than the 21-chloro substituent leads to a toxic compound, whereas the 21-fluoro substituent gives only a moderately active compound.

The invention, therefore, concerns the 21-chloro-pregnane derivative of the formula

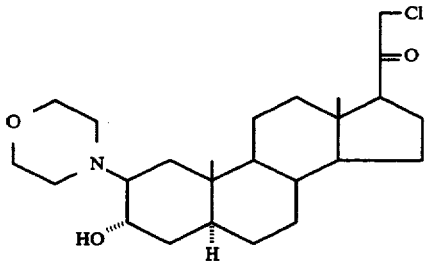

or pharmaceutically acceptable salts thereof.

The 21-chloro-pregnane derivative of this invention can be prepared by treating the corresponding 21-"leaving group" derivative with a chloride containing agent, after which the compound obtained is optionally converted into a pharmaceutically acceptable salt. The compounds of formula I, wherein $R_1$ is morpholino, $R_2$ is $H_2$, and $R_3$ is a leaving group are suitable starting materials. The leaving group is a group commonly in use for substitution by a nucleophile. Examples are halogens, particularly iodine and bromine, methylsulfonate (mesyl), and p-toluenesulfonate (tosyl). Chloride containing agents are preferably salts containing the anion $Cl^-$. Suitable chloride containing agents are sodium, potassium, and lithium chloride, which can be applied in (for example) 1-methyl-2-pyrrolidinone or a mixture of water and a lower alcohol as solvent.

Alternatively the 21-chloro compound can also be prepared by treatment of the corresponding 20-(hydroxyethyl)imino pregnane or a similar imino pregnane derivative with N-chlorosuccinimide, and, if desired, converted into a salt.

The novel 21-chloro-pregnane derivative may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the invention may be administered enterally or parenterally, and for humans preferably in a daily dosage of 0,001-10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may by means of pharmaceutically suitable liquids be applied as an injection preparation in the form of a solution, suspension, or emulsion. The compounds are preferably administered intravenously.

The invention is further illustrated by the following examples.

EXAMPLE 1

(2β,3α,5α)-21-chloro-3-hydroxy-2-(4-morpholinyl)-pregnan-20-one

To a flask fitted with a water separator 10 g of (2β,3α,5α)-3-hydroxy-2-(4-morpholinyl)pregnan-20-one, prepared according to British Patent 1,039,441, 50 ml of ethanolamine, 250 ml of toluene, and 1 g of Dowex 50-W were added. The mixture was heated under reflux for 5 h, whereupon approximately 16 ml of a solution of ethanolamine and water had collected in the water separator. After hot filtration and cooling, the precipitated solid was washed with hexane, dissolved in dichloromethane, washed with water and dried over sodium sulfate. The solvent was removed and the solid recrystallized from ethanol to give 9.1 g of (2β,3α,5α)-20-[2-(hydroxyethyl)imino]-2-(4-morpholinyl)pregnan-3-ol. To 5.3 g of this imino derivative in 106 ml of tetrahydrofuran were added 1.6 g of N-chlorosuccinimide. The solution was stirred for 2 h at room temperature, and 38 ml of 1M hydrochloric acid were added. Stirring was continued for another 2 h and the reaction mixture was poured into 1 l of water. Aqueous sodium carbonate was added until the pH exceeded 9.0 and the precipitated solid was filtered, washed with water and dissolved in dichloromethane. The solution was dried over sodium sulfate, the solvent removed, and the residue crystallized from methanol to give 3.9 g of (2β,3α,5α)-21-chloro-3-hydroxy-2-(4-morpholinyl)pregnan-20-one. m.p. 181° C.; $[α]_D^{20} = +160°$ (c 0.81, chloroform).

EXAMPLE 2

To a stirred suspension of 100 g of (2β,3α,5α)-3-hydroxy-2-(4-morpholinyl)pregnan-20-one, prepared according to British Patent 1,039,441, in 2.5 l of methanol were added 81 ml of 3M methanolic hydrogen chloride and 10 ml of acetyl chloride. Bromine (16.6 ml) in 1 l of methanol was added dropwise over 1.5 h. The mixture was stirred at room temperature for a further 20 min and then poured into 18 l of water. Aqueous sodium carbonate solution was added until the pH exceeded 9.0 and the precipitated solid was filtered, washed with water and dissolved in dichloromethane. The solution was dried over sodium sulfate, the solvent removed, and the residue crystallized from acetone-hexane to give 46 g of (2β,3α,5α)-21-bromo-3-hydroxy-2-(4-morpholinyl)pregnan-20-one. 5.0 g of this 21-bromo compound were dissolved in 50 ml of 1-methyl-2-pyrrolidinone and 2.5 g of lithium chloride were added. The mixture was stirred at 80° C. under nitrogen for 2 h, cooled to room temperature and poured into 500 ml of water. The precipitated solid was filtered off, washed with water and dissolved in dichloromethane. The solution was dried over sodium sulfate, the solvent removed, and the residue crystallized from acetone-hexane to give 2 g of (2β,3α,5α)-21-chloro-3-hydroxy-2-(4-morpholinyl)pregnan-20-one as in Example 1.

EXAMPLE 3

The 21-bromo compound of Example 2 can also be converted into (2β,3α,5α)-21-acetoxy-3-hydroxy-2-(4-morpholinyl)-pregnan-20-one, m.p. 157° C.; $[α]_D^{20} = +151°$ (c 0.78, chloroform), by treatment with potassium acetate and potassium iodide in a mixture of dimethylformamide and acetic acid. Using a saturated solution of potassium carbonate in methanol this 21-acetoxy derivative is hydrolyzed to (2β,3α,5α)-3,21-dihydroxy-2-(4-morpholinyl)pregnan-20-one. m.p. 199° C.; $[α]_D^{20} = +143°$ (c 0.88, chloroform). To 1 g of this compound in 8.7 ml of pyridine were added 0.9 ml of methanesulfonyl chloride at −40° C. and the mixture was maintained at this temperature for 7 min. The solution was poured into 100 ml of water. Aqueous sodium carbonate solution was added until the pH exceeded 9.0 and the supernatant was decanted, the residue washed with water and dissolved in dichloromethane. The solution was dried over sodium sulfate, the solvent removed and the crude product treated with lithium chloride in 1-methyl-2-pyrrolidinone for 1.5 h at 50° C. After usual work-up (2β,3α,5α)-21-chloro-3-hydroxy-2-(4-morpholinyl)pregnan-20-one as in Example 1 was obtained.

I claim:

1. A 21-chloro-pregnane derivative of the formula

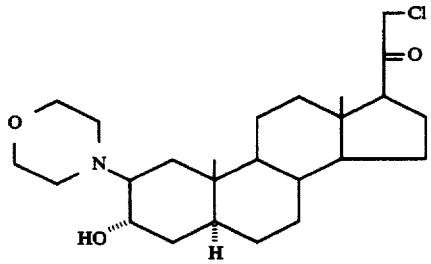

and pharmaceutically acceptable salts thereof.

2. A method for inducing anesthesia in a patient comprising administering an anesthetically effective amount of the 21-chloro-pregnane derivative of claim 1.

3. A pharmaceutical composition comprising an effective amount of the 21-chloro-pregnane derivative of claim 1 for inducing an anesthetic effect in a patient and pharmaceutically acceptable auxiliaries.

* * * * *